(12) United States Patent
Messier et al.

(10) Patent No.: US 9,678,322 B2
(45) Date of Patent: Jun. 13, 2017

(54) SYSTEM AND METHOD FOR DATING TEXTURED GELATIN SILVER PAPER

(71) Applicants: Paul Messier, Brighton, MA (US); Andrew Messier, Stow, MA (US)

(72) Inventors: Paul Messier, Brighton, MA (US); Andrew Messier, Stow, MA (US)

(*) Notice: Subject to any disclaimer, the term of this patent is extended or adjusted under 35 U.S.C. 154(b) by 410 days.

(21) Appl. No.: 14/333,647

(22) Filed: Jul. 17, 2014

(65) Prior Publication Data

US 2015/0077536 A1    Mar. 19, 2015

Related U.S. Application Data

(60) Provisional application No. 61/860,844, filed on Jul. 31, 2013.

(51) Int. Cl.
| | |
|---|---|
| *H04N 7/18* | (2006.01) |
| *G02B 21/00* | (2006.01) |
| *G06K 9/46* | (2006.01) |
| *G06K 9/00* | (2006.01) |
| *G06K 9/20* | (2006.01) |
| *H04N 5/235* | (2006.01) |
| *G01N 21/86* | (2006.01) |
| *G03B 15/07* | (2006.01) |

(52) U.S. Cl.
CPC ....... *G02B 21/008* (2013.01); *G06K 9/00577* (2013.01); *G06K 9/2036* (2013.01); *G06K 9/4604* (2013.01); *G01N 2021/8618* (2013.01); *G03B 15/07* (2013.01); *H04N 5/2354* (2013.01)

(58) Field of Classification Search
CPC .................. G02B 21/008; G03B 15/07; G01N 2021/8618; G06K 9/00577; G06K 9/2036; G06K 9/4604; H04N 5/2354
USPC ......................................................... 348/80
See application file for complete search history.

(56) References Cited

U.S. PATENT DOCUMENTS

| | | | |
|---|---|---|---|
| 2001/0040225 A1* | 11/2001 | Kodama | G01B 11/028 250/559.36 |
| 2006/0132496 A1* | 6/2006 | Horton | G06T 11/40 345/582 |

* cited by examiner

*Primary Examiner* — Allen Wong

(57) ABSTRACT

A system and method for dating gelatin silver photographic paper is provided. The system and method includes providing a database management system having physical texture characteristic profiles. The system implements a program of instructions to determine a probable date range or source for each textural characteristic profile. The system includes LED sources disposed around an inner surface of a dome; an LED controller, and a CCD imager microscope.

13 Claims, 4 Drawing Sheets

SYSTEM AND METHOD FOR DATING TEXTURED GELATIN SILVER PAPER

CROSS-REFERENCE TO RELATED APPLICATIONS

The present application is related to, claims the earliest available effective filing date(s) from (e.g., claims earliest available priority dates for other than provisional patent applications; claims benefits under 35 USC §119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith:

U.S. provisional patent application 61/860,844 entitled "A System and Method for Dating Textured Gelatin Silver Paper", naming Paul Messier and Andrew Messier as inventors, filed 31 Jul. 2013.

BACKGROUND

1. Field of Use

These teachings relate generally to forensic photograph dating and more particularly to systems employing digital computers for determining the probabilistic date of a physical characteristic associated with a photograph. The teachings may also relate to any field where reflectance transformation imaging is employed, such as, for example, the fields of ballistics investigation or numismatics.

2. Description of Prior Art (Background)

A photographic print's date is elementary to the understanding of the work, its historical context and the photographer's artistic intent. It carries implications for its treatment, display and storage and can manifestly influence its market value. Recently, photographs have become the target of forgers, and as the market value of these works increase, so will forgery continue. The detection of forged photography is particularly difficult in the context of today's imaging technology as experts must be able to tell the difference between originals and reprints. For example, a forger in possession of photo-negatives would allow the forger to print an unlimited number of prints, which then can be passed off as original.

Texture is a defining attribute of photographic paper. Starting in the early 20th century, manufacturers manipulated texture to differentiate their products and to satisfy the aesthetic and functional requirements of photographers. Prior to WWII, when black and white silver gelatin paper was the dominant photographic medium, dozens of manufacturers worldwide produced a wide array of surfaces. From this period a book of specimen prints by the Belgian company Gevaert lists twenty five different surfaces comprising combinations of texture, reflectance, color and paper thickness (Gevaert Company of America c. 1935). Around the same time, a sample book from the Defender Company of Rochester N.Y. lists twenty seven surfaces (Defender Photo Supply Company c. 1935), Mimosa twenty six (Mimosa AG c. 1935) and Kodak twenty two (Eastman Kodak c. 1935). Each listed surface was proprietary to the different manufacturers and each was used across their multiple brands of paper with changes, additions, and deletions occurring over a span of many years.

Texture, a vital factor in the evaluation of paper surface, impacts the visibility of fine detail and thus provides insight into the artistic intent of the photographer and the envisioned purpose of a particular print. For example, prints intended for reproduction or documentary functions tend to be better suited on smooth-surface papers that render details with sharpness and clarity; on the other hand, more impressionistic or expressive subjects, especially those depicting large unmodulated masses of shadows or highlights, are best suited for papers with rough, broadly open textures (Eastman Kodak Company c. 1935).

A result of a careful and deliberate manufacturing process, texture applied to silver gelatin paper is designed to be distinct and distinguishable through processing and post-processing procedures. Given these texture attributes, an encyclopedic collection of surface textures can reveal vital clues about a photographic print of unknown origin. Likewise a method for classifying textures can provide a means to link prints to specific photographers or to other prints of known provenance.

Since the composition of photographic paper was frequently changed, fake photographs are likely to be printed on modern photographic paper or photographic paper not contemporaneous with the original photograph. Therefore, there is a need for a system to non-destructively date photographic paper.

Determining photographic paper surface texture, a critical feature in the manufacture, marketing and use of photographic paper, is one way to non-destructively date photographic paper. Using a raking light can reveal texture through a stark rendering of highlights and shadows. Though raking light photomicrographs effectively document surface features of photographic paper, the sheer number and diversity of textures used for historic papers prohibits efficient visual classification.

In addition, the raking light may be applied to a sample paper with different angles of incidence and different intensities, thereby rendering different highlights and shadows for the same photograph or sample. Therefore, a need exists for a method and apparatus for standardizing and classifying photograph textures revealed by a raking light.

BRIEF SUMMARY

The foregoing and other problems are overcome, and other advantages are realized, in accordance with the presently preferred embodiments of these teachings.

The invention is directed towards a system for extracting texture features from a sample under investigation. The system includes a dome, wherein the dome comprises a plurality of LED rings disposed around an inner surface of the dome. The system also includes a LED controller for controlling the plurality of LEDs and the incident light impinging upon the sample situated within the dome. Also included is a CCD imager microscope and controller for capturing LED light reflected from the sample. The invention also includes a computer system for storing and analyzing the texture features from the sample. The computer system includes a processor for executing instructions; a display, operatively coupled to the processor; an input communications device; and a computer readable medium, operatively coupled to the processor. The computer readable medium contains a set of system instructions that, if executed by the processor, are operable to cause the computer system to construct a rules engine, the rules engine comprising texture identification rules and resources to classify the texture features.

The invention is also directed towards a system for extracting texture features from a sample under investigation. The system includes a plurality of light emitting diodes (LEDs) disposed semi-spherically around the sample, wherein the plurality of LEDs are arranged to form a plurality of LED rings and wherein each LED ring comprises a unique angle/distance pairing with respect to the sample.

In another embodiment the invention is directed towards a system for extracting texture features from a sample under investigation. The system includes a dome for enclosing the sample. The dome includes a plurality of light emitting diodes (LEDs) arranged to form a plurality of LED rings around the inner surface of the dome. The system also includes an LED controller for controlling the plurality of LEDs; a CCD imager microscope for capturing LED light reflected from the texture features inherent within the sample; and a charge coupled device (CCD) imager microscope controller for controlling the CCD imager microscope. In addition, the system includes a computer system for electronically storing and analyzing the texture features from the sample. The computer system includes a processor for executing instructions; a display, operatively coupled to the processor; and a computer readable medium, operatively coupled to the processor. The computer readable medium contains a set of system instructions that, if executed by the processor, are operable to cause the computer system to construct a rules engine, the rules engine comprising texture identification rules and resources to classify the texture features. The computer readable medium also contains a second set of system instructions that, if executed by the processor, are operable to cause the computer system to capture a plurality of texture datasets associated with the sample, wherein one of the plurality of texture datasets comprise a first set of texture features and a second one of the plurality of texture datasets comprise a second set of texture features. The datasets may be captured at the same time with different LED control settings and/or at different times with identical LED control settings.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example; and If the specification states a component or feature "may," "can," "could," "should," "preferably," "possibly," "typically," "optionally," "for example," or "might" (or other such language) be included or have a characteristic, that particular component or feature is not required to be included or to have the characteristic.

Figure 1:
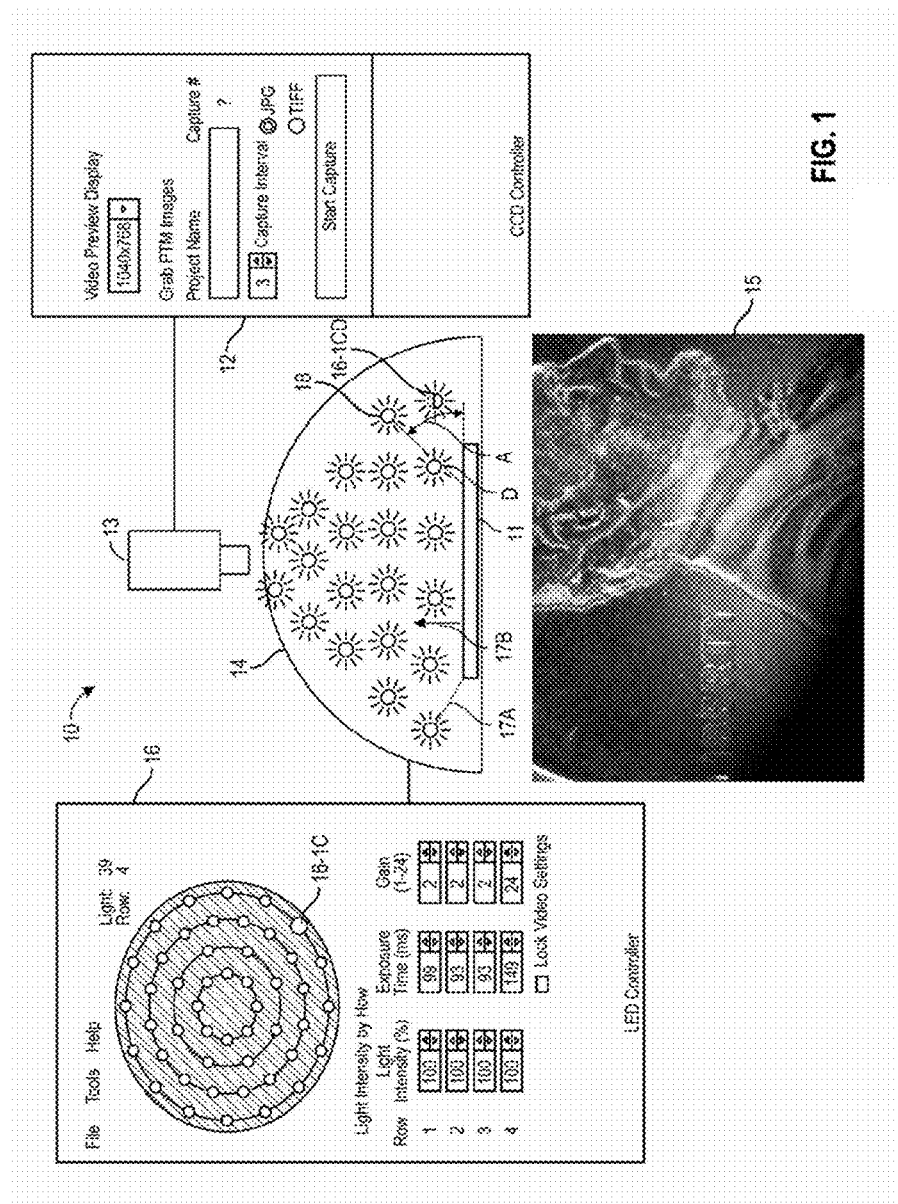
FIG. 1 is a pictorial illustration of a system configuration of an embodiment of the present invention.

Referring to FIG. 1 there is shown a pictorial illustration of a system configuration of an embodiment of the present invention 10 for applying a raking light 17A to a sample 11 under investigation and subsequently imaging the reflected raking light 17B with a microscope and CCD imager 13. The raking light 17A is emitted from one or more LEDs 18 arranged around the perimeter of dome 14. It will be understood that each of the LEDs may comprise a unique angle A and/or distance D from sample 11.

FIG. 1 shows a single LED 16-1 illuminated within an array of a plurality of light emitting diodes (LEDs) 18 mounted to lighting array dome or semi-sphere 14. It will be appreciated that any number of LEDs may be used, such as for example 48 LEDs. It will also be appreciated that the LEDs may emit any suitable color or spectrum. The lighting array dome 14 includes the plurality of LEDs coupled to the LED controller 16 through a printed circuit board (PCB). The LED controller 16 provides an inter-face to address each LED 18 and controls: illumination intensity of each LED, on/off sequence of each LED with respect to the other LEDs, and exposure or energized state time of each LED. It will be appreciated that each LED comprises a static angle and distance to a reference point, e.g., a test sample, and each LED comprises dynamic illumination intensity, exposure time, gain, and sequencing. It will also be appreciated the LEDs may be arranged geometrically such as, for example, in LED rows around the inside of the lighting array dome 14. And, each row may comprise a unique angle/distance pair with respect to sample 11.

Also shown is CCD controller 12 to control key CCD functions including image capture, white balance, image output (file creation) and gain (light sensitivity of the sensor).

Still referring to FIG. 1, an image 15 of the illuminated sample 11 is shown. As shown, the raking light 17A illuminates the sample 11 from, in this example, an oblique angle, thus highlighting certain features of the sample 11 under investigation.

The dot in the graphical user interface (GUI) corresponds with the LEDs illuminated in the dome. For example, dot 16-1c corresponds to LED 16-1. Each of the LEDs, can be preset for desired illuminating while examining the impact of the illumination using a preview image to determine light intensity and other camera related exposure options. Once set, the LEDs are energized in a predetermined sequence with the corresponding raking images automatically captured and save by CCD imager 13 and CCD controller 12. It will be understood that any suitable number of LEDs may be energized. It will also be appreciated that all LED and CCD settings may be captured to precisely repeat the LED illumination.

Figure 2:
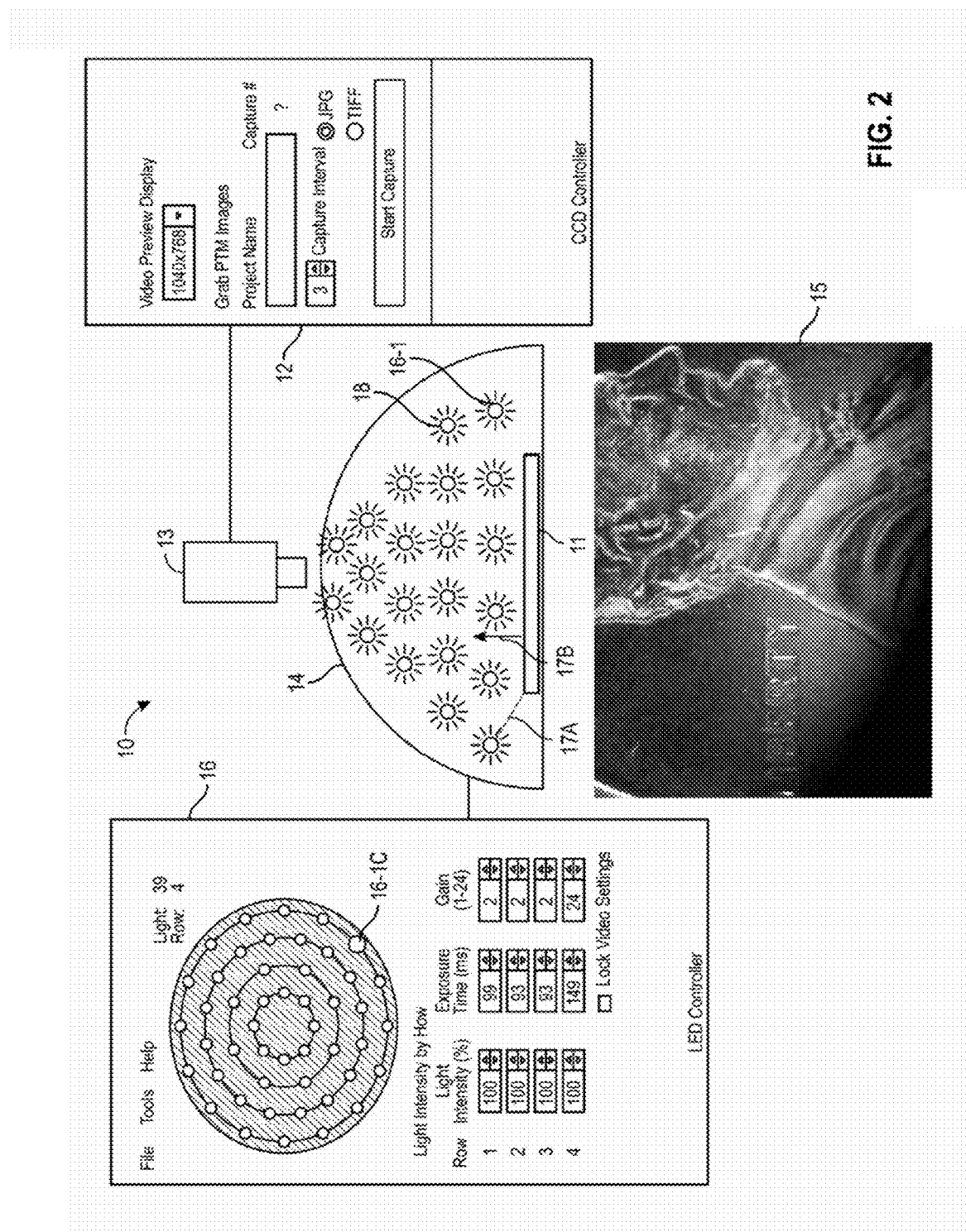
FIG. 2 is a pictorial illustration of an alternate state of the system configuration of the present invention shown in FIG. 1.

Referring also to FIG. 2 for comparison this illustration shows a different position of an illuminated LED and the corresponding dot 16-2c in the controller 16 window. Of note is the effect of the different angle of raking light illumination 24A on the sample 11.

Still referring to FIG. 2, an image 22 of the illuminated sample 11 is shown. As shown, the raking light 24A illuminates the sample 11 from, in this example, a perpendicular angle, thus highlighting certain features of the sample 11 under investigation that are not readily apparent from a raking light of a different intensity or incident angle (compare item 22 with FIG. 1, item 15).

Figure 3:
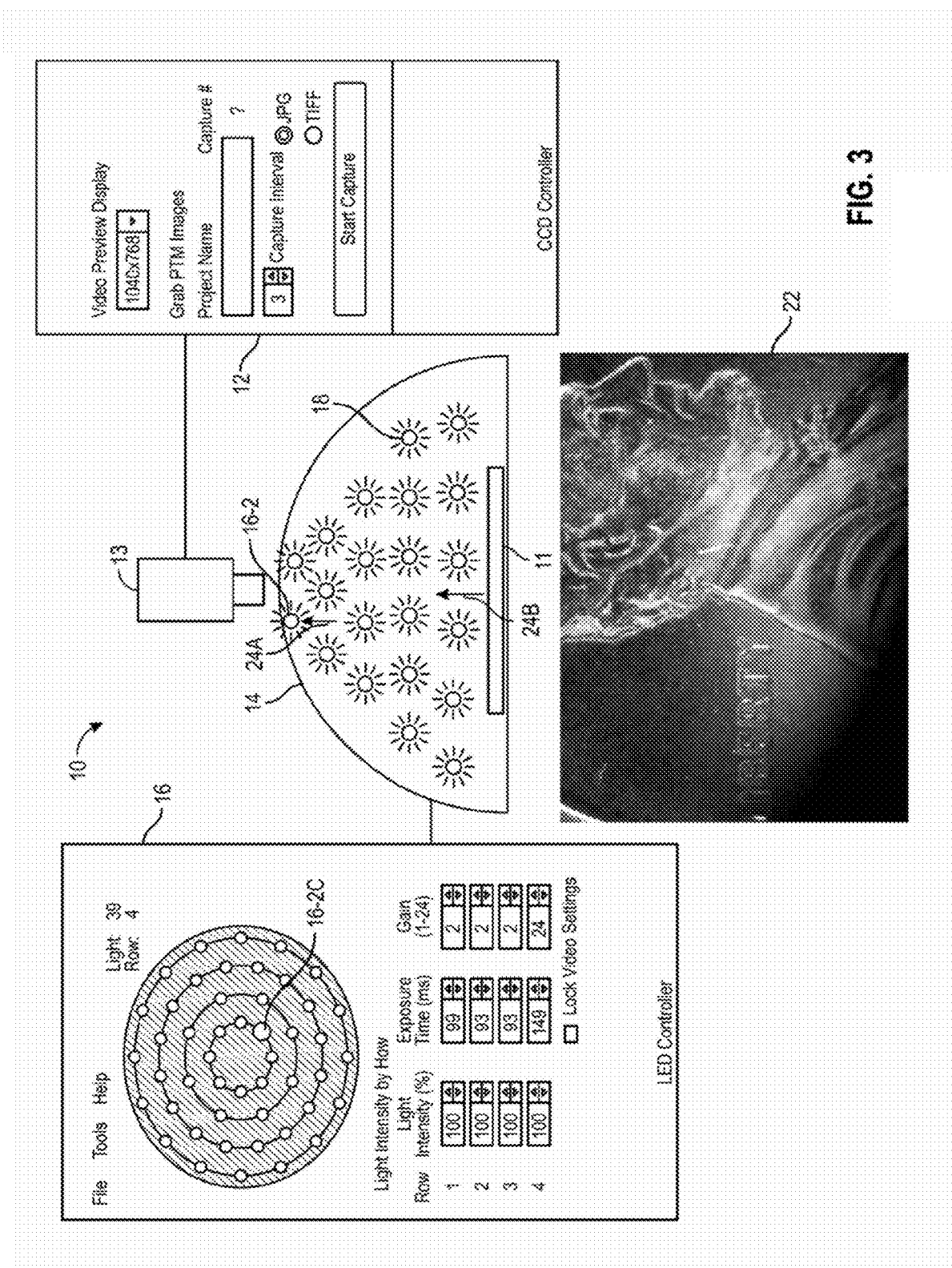
FIG. 3 is a pictorial illustration of a third alternate state of the system configuration of the present invention shown in FIG. 1.

Referring also to FIG. 3 for yet another comparison, this illustration shows a different position of an illuminated LED 16-3 and the corresponding dot 16-3c in the controller 16 window. Of note is the effect of the different angle of illumination on the sample 11 shown in image 32 (compare with FIG. 2, item and with FIG. 1, item 15).

Still referring to FIG. 3, an image 32 of the illuminated sample 11 is shown. The raking light from LED 16-3 illuminates the sample 11 from, in this example, another angle, thus highlighting certain features of the sample 11 under investigation that are not readily apparent from a raking light of a different intensity or incident angle.

It will be understood that the present invention advantageously provides an ability to precisely control the lighting angle and intensity and allow a repeatable way to examine and document surface features under different lighting conditions. The one or more images shown in FIG. 1-FIG. 3 may be captured as a texture dataset (See FIG. 4, 414) for subsequent processing and comparison. For example, a texture dataset, as described herein, of a photograph, or painting, may be compared with later, or earlier captured texture datasets of the photograph or painting to determine deterioration rates, identity, and authenticity. Similarly, texture datasets, as described herein, of a painting or photograph may be compared with one or more standard texture datasets, as described herein, of known characteristics such as, for example, texture and surface composition.

It will be appreciated that the texture dataset of a sample described herein comprises a static or dynamic raking image. It will be understood that the static raking image is a function of the number of energized LEDs and each LED's angle and distance to the sample, and each LED's preset intensity and gain. It will be further understood that the dynamic raking image is a function of the aforementioned factors and LED exposure time and the LED's energizing or exposure sequence.

Figure 4:
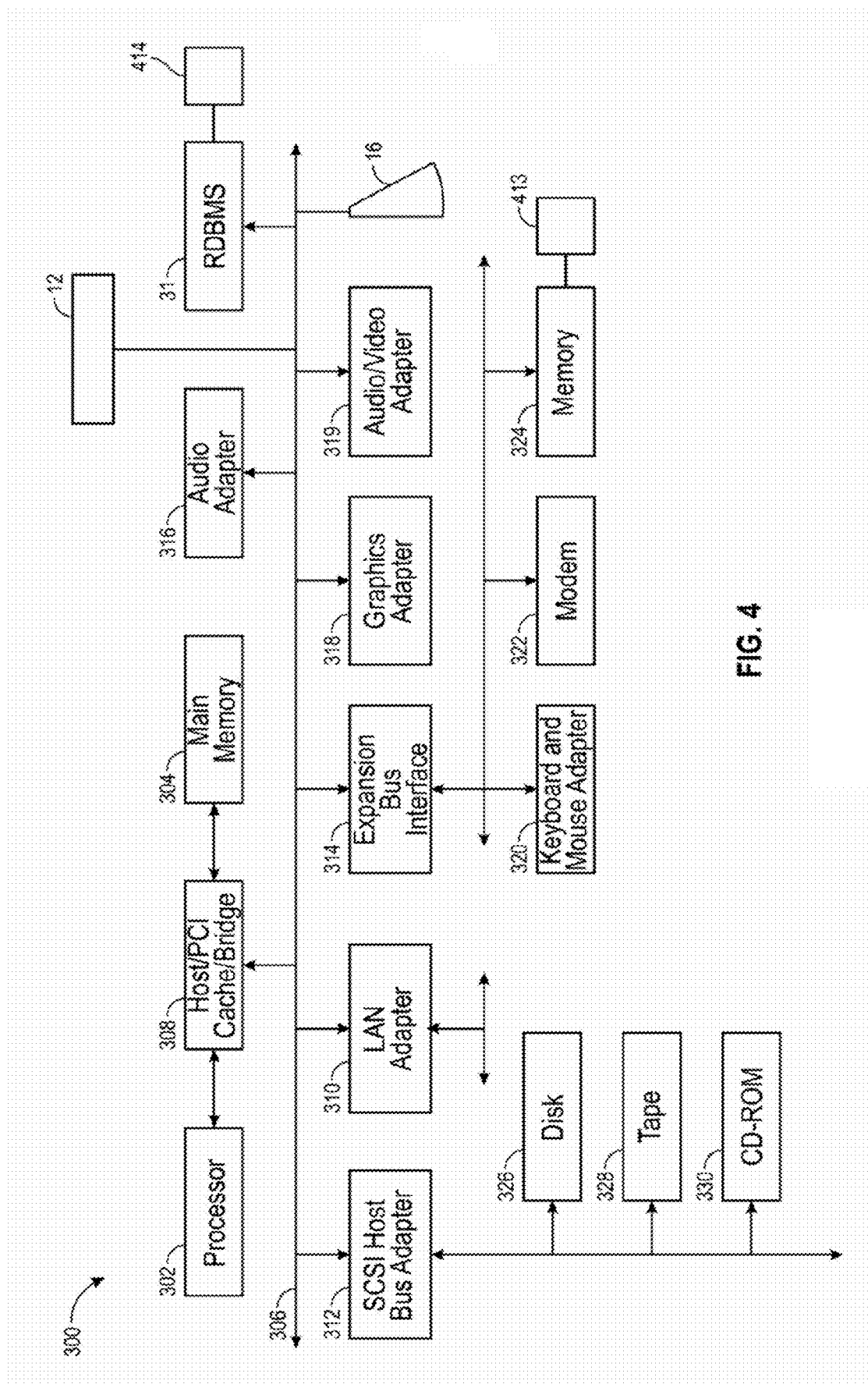
FIG. 4 is a block diagram of computer architecture for implementing the system configurations shown in FIG. 1-FIG. 3.

With reference also to FIG. 4, a block diagram illustrating a computer architecture 300 for LED controller 16 incidence parameters and the CCD controller 12 is shown. System 300 employs a peripheral component interconnect (PCI) local bus architecture. Although the depicted example employs a PCI bus, other bus architectures such as Accelerated Graphics Port (AGP) and Industry Standard Architecture (ISA) may be used. Processor 302 and main memory 304 are connected to PCI local bus 306 through PCI bridge 308. PCI bridge 308 also may include an integrated memory controller and cache memory for processor 302. Additional connections to PCI local bus 306 may be made through direct component interconnection or through add-in boards.

In the depicted example, local area network (LAN) adapter 310, SCSI host bus adapter 312, and expansion bus interface 314 are connected to PCI local bus 306 by direct component connection. It will be understood that LAN adapter 310 may also include an internet browser. In contrast, audio adapter 316, graphics adapter 318, and audio/video adapter 319 are connected to local bus 306 by add-in boards inserted into expansion slots. Local bus may be any suitable bus architecture such as, for example, PCI or USB. Expansion bus interface 314 provides a connection for a keyboard and mouse adapter 320, modem 322, and additional memory 324. Small computer system interface (SCSI) host bus adapter 312 provides a connection for hard disk drive 326, tape drive 328, and CD-ROM drive 330. Typical PCI local bus implementations will support PCI expansion slots or add-in connectors.

An operating system runs on processor 302 and is used to coordinate and provide control of various components within data processing system 31. Data processing sa processing system 31 may be configured to process dataset 414 as described herein. The operating system may be any suitable commercially available operating system. In addition, an object oriented programming system such as Java may run in conjunction with the operating system and provide calls to the operating system from Java programs or applications executing on data processing system 300. "Java" is a trademark of Sun Microsystems, Inc. Instructions for the operating system, the object-oriented operating system, and applications or programs are located on storage devices, such as hard disk drive 326, and may be loaded into main memory 304 for execution by processor 302.

System 300 may be configured to regressively cluster texture dataset 414 to allocate data points within the dataset to a probable date range or a comparison confidence factor. In some embodiments, such an adaptation may be incorporated within system 300. In particular, system 300 may include storage medium 324 with program instructions 413 executable by processor 302 to regressively cluster dataset 414. In an embodiment in which dataset 414 is external to system 300, however, the adaptation to regressively cluster dataset 414 may be additionally, or alternatively, incorporated within the respective data source/s of dataset 414. In particular, the data source/s of dataset 414, in such an embodiment, may include a storage medium with program instructions which are executable through a processor for regressively clustering data.

In general, input may be transmitted to system 300 to execute program instructions 413 within storage medium 324. Storage medium 324 may include any device for storing program instructions, such as, for example, a read-only memory, a random access memory, a magnetic or optical disk, or a magnetic tape. Program instructions 413 may include any instructions by which to perform any suitable method or regression clustering and classification processes. In particular, program instructions 413 may include instructions for correlating variable parameters of a dataset and other instructions for clustering the dataset through the iteration of a regression algorithm. In this manner, program instructions 413 may used to generate a plurality of different functions correlating variable parameters of a dataset.

In addition, program instructions 413 may include instructions for determining directives by which to classify new data into the dataset with respect to the generated functions. In some cases, program instructions 13 may further include instructions by which to receive new data and predict values of variable parameters associated with the new data and dataset.

For example, the computer readable medium may contain a set of system instructions that, if executed by the processor 302, are operable to cause the computer system 300 to capture a plurality of texture datasets associated with the sample 11; where each of the texture datasets may be captured at different times or under different conditions. In this manner the comparisons may be used to determine degradation or authenticity.

Similarly, the computer readable medium may contain a set of system instructions that, if executed by the processor 302, are operable to cause the computer system 300 to generate a baseline texture dataset. The baseline texture dataset may be generated according to a predetermined formula or determined empirically with a sample having known characteristics.

Those of ordinary skill in the art will appreciate that the hardware in FIG. 1 through FIG. 4 may vary depending on the implementation. Other internal hardware or peripheral devices, such as flash read-only memory (ROM), equivalent nonvolatile memory, or optical disk drives and the like, may be used in addition to or in place of the hardware depicted in FIG. 1-FIG. 4.

The depicted example in FIG. 1-FIG. 4 and above-described examples are not meant to imply architectural limitations. For example, system 300 also may be a notebook computer or hand held computer in addition to taking the form of a PDA.

It should be understood that the foregoing description is only illustrative of the invention. Thus, various alternatives and modifications can be devised by those skilled in the art without departing from the invention. Accordingly, the present invention is intended to embrace all such alternatives, modifications and variances that fall within the scope of the appended claims.

What is claimed is:

1. A system for extracting texture features from a sample under investigation, the system comprising:
   a computer system for storing and analyzing the texture features from the sample, the computer system comprising:
      a processor for executing instructions;
      a display, operatively coupled to the processor;
      an input communications device;
      a non-transitory computer readable medium, operatively coupled to the processor, wherein the non-transitory computer readable medium contains:
         a set of system instructions that, if executed by the processor, are operable to cause the computer system to construct a rules engine, the rules engine comprising texture identification rules and resources to classify the texture features; and
         a fourth set of system instructions that, if executed by the processor, are operable to cause the computer system to define at least one baseline texture dataset;
   a dome for enclosing the sample, wherein the dome comprises:
      a plurality of light emitting diodes (LEDs) disposed around an inner surface of the dome, wherein the plurality of LEDs are arranged to form a plurality of LED rings around the inner surface of the dome;
   an LED controller for controlling the plurality of LEDs;
   a CCD imager microscope for capturing LED light reflected from the texture features inherent within the sample; and
   a CCD imager microscope controller for controlling the CCD imager microscope.

2. The system as in claim 1 wherein the LED controller controls each of the LEDs light intensity independently of the other LEDs.

3. The system as in claim 1 wherein the LED controller controls each of the LEDs exposure time independently of the other LEDs.

4. The system as in claim 1 wherein the LED controller controls each of the LEDs gain independently of the other LEDs.

5. The system as in claim 1 wherein each of the LED rings comprise a unique angle/distance pairing with respect to the sample.

6. The system as in claim 1 wherein the non-transitory computer readable medium further contains:
   a second set of system instructions that, if executed by the processor, are operable to cause the computer system to capture a plurality of texture datasets associated with the sample, wherein one of the plurality of texture datasets comprise a first set of texture features and a second one of the plurality of texture datasets comprise a second set of texture features.

7. The system as in claim 6 wherein the non-transitory computer readable medium further contains:
   a third set of system instructions that, if executed by the processor, are operable to cause the computer system to compare the plurality of texture datasets associated with the sample and identify differences between the plurality of texture datasets.

8. The system as in claim 1 wherein the non-transitory computer readable medium further contains:
   a fifth set of system instructions that, if executed by the processor, are operable to cause the computer system to compare the texture features associated with the sample and identify differences between the texture features and the at least one baseline texture dataset.

9. A system for extracting texture features from a sample under investigation, the system comprising:
   a dome for enclosing the sample, wherein the dome comprises:
      a plurality of light emitting diodes (LEDs) disposed around an inner surface of the dome, wherein the plurality of LEDs are arranged to form a plurality of LED rings around the inner surface of the dome;
   an LED controller for controlling the plurality of LEDs;
   a CCD imager microscope for capturing LED light reflected from the texture features inherent within the sample;
   a CCD imager microscope controller for controlling the CC imager microscope;
   a computer system for storing and analyzing the texture features from the sample, the computer system comprising:
      a processor for executing instructions;
      a display, operatively coupled to the processor;
      a non-transitory computer readable medium, operatively coupled to the processor, wherein the computer readable medium contains:
         a set of system instructions that, if executed by the processor, are operable to cause the computer system to construct a rules engine, the rules engine comprising texture identification rules and resources to classify the texture features;
         a second set of system instructions that, if executed by the processor, are operable to cause the computer system to capture a plurality of texture datasets associated with the sample, wherein one of the plurality of texture datasets comprise a first set of texture features and a second one of the plurality of texture datasets comprise a second set of texture features; and a third set of system instructions that, if executed by the processor, are operable to cause the computer system to compare the plurality of texture datasets associated with the sample and identify differences between the plurality of texture datasets.

10. The system as in claim 9 wherein the non-transitory computer readable medium further contains:

a fourth set of system instructions that, if executed by the processor, are operable to cause the computer system to define at least one baseline texture dataset; and a fifth set of system instructions that, if executed by the processor, are operable to cause the computer system to compare the texture features associated with the sample and identify differences between the texture features and the at least one baseline texture dataset.

11. The system as in claim 9 wherein the LED controller controls each of the LEDs light intensity, exposure time, and gain independently of the other LEDs.

12. A The system as in claim 9 wherein each of the LED rings comprise a unique angle/distance pairing with respect to the sample.

13. A system for extracting texture features from a sample under investigation, the system comprising:

a computer system for storing and analyzing the texture features from the sample, the computer system comprising:
  a processor for executing instructions;
  a display, operatively coupled to the processor;
  an input communications device;
  a non-transitory computer readable medium, operatively coupled to the processor, wherein the non-transitory computer readable medium contains:
    a set of system instructions that, if executed by the processor, are operable to cause the computer system to construct a rules engine, the rules engine comprising texture identification rules and resources to classify the texture features:
    a second set of system instructions that, if executed by the processor, are operable to cause the computer system to capture a plurality of texture datasets associated with the sample, wherein one of the plurality of texture datasets comprise a first set of texture features and a second one of the plurality of texture datasets comprise a second set of texture features; and a third set of system instructions that, if executed by the processor, are operable to cause the computer system to compare the plurality of texture datasets associated with the sample and identify differences between the plurality of texture datasets;

an LED controller for controlling the plurality of LEDs, wherein the LED controller controls each of the LEDs light intensity, exposure time, and gain independently of the other LEDs;

a CCD imager microscope for capturing LED light reflected from the texture features inherent within the sample; and a CCD imager microscope controller for controlling the CCD imager microscope; and a plurality of light emitting diodes (LEDs) disposed semi-spherically around the sample, wherein the plurality of LEDs are arranged to form a plurality of LED rings and wherein each LED ring comprises a unique angle/distance pairing with respect to the sample.

* * * * *